United States Patent [19] [11] Patent Number: 4,794,169
Elgjo et al. [45] Date of Patent: Dec. 27, 1988

[54] PENTAPEPTIDES WITH CELL GROWTH REGULATORY EFFECTS AND A PROCESS FOR THE PREPARATION THEREOF

[75] Inventors: Kjell Elgjo; Karl-Ludvig Reichelt, both of Oslo, Norway

[73] Assignee: Bio-Tech A/S, Oslo, Norway

[21] Appl. No.: 30,959

[22] PCT Filed: Jun. 18, 1986

[86] PCT No.: PCT/NO86/00041

§ 371 Date: Feb. 18, 1987

§ 102(e) Date: Feb. 18, 1987

[87] PCT Pub. No.: WO87/00180

PCT Pub. Date: Jan. 15, 1987

[30] Foreign Application Priority Data

Jun. 26, 1985 [NO] Norway ................... 852564
Feb. 28, 1986 [NO] Norway ................... 860752

[51] Int. Cl.$^4$ ............................................ C07K 7/06
[52] U.S. Cl. ................................................... 530/330
[58] Field of Search ........................................ 530/330

[56] References Cited

PUBLICATIONS

Elgjo et al., Cell Biology International Reports, vol. 8, No. 5, pp. 379–382 (5/1984).
Elgjo et al., Chem. Abstr. vol. 101, No. 66833j (1984).
Elgjo et al., Chem. Abstr. vol. 106, No. 79315v (1987) (Abstract of Serono Symp. Publ. Raven Press 34 pp. 259γ, 1986).
Elgjo et al., Chem. Abstr. vol. 105, No. 219705d (1986) (Abstract of J. Invest. Dermatol. 87(5), pp. 555–8, 1986).

Primary Examiner—Delbert R. Phillips
Assistant Examiner—Christina Chan
Attorney, Agent, or Firm—Wenderoth, Lind & Ponack

[57] ABSTRACT

New pentapeptide of the formula

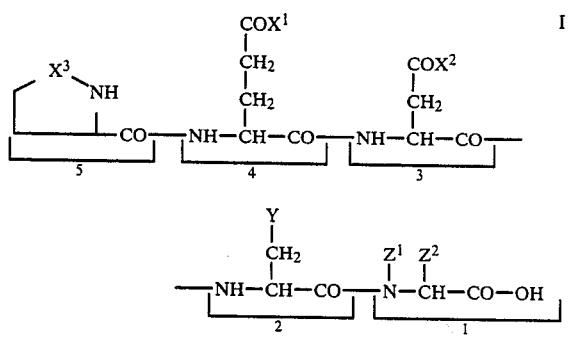

in which
$X^1$ and $X^2$ are the same or different and are OH or $NH_2$,
Y is H or OH,
$X^3$ is CO or $CH_2$,
one of the groups $Z^1$ and $Z^2$ is H and the other is H or $CH_3$,
all the amino acid unit being in L-configuration, with the exception that the C-terminal amino acid unit is in D-configuration when $Z^2$ is methyl,
and the C-terminal carboxyl group may be reduced to —$CH_2$—OH or be in amide form, and cation complexes and salts thereof.

The pentapeptide may be prepared by subjecting a protected derivative thereof to deprotection.

The pentapeptide has cell growth regulatory activity.

4 Claims, No Drawings

PENTAPEPTIDES WITH CELL GROWTH REGULATORY EFFECTS AND A PROCESS FOR THE PREPARATION THEREOF

The present invention relates to new pentapeptides which reversibly inhibit cell proliferation in squamous epithelia, and a process for preparing such pentapeptides.

Many skin detectors are characterized by an abnormally fast rate of cell proliferation in the epidermis. In this category of skin diseases, psoriasis is the one which has been best investigated. Here, cell proliferation takes place very rapidly, and the cells do not have sufficient time to mature normally and are shed from the surface still containing the cell nucleus. In many other skin diseases the cell proliferation rate is markedly increased, but none of these have been subjected to such extensive studies as has psoriasis. High mitotic activity is also found in most benign and malignant skin tumors of epidermal origin.

Cell division (mitosis) in the normal epidermis is confined to the lowermost cell layer (the basal cell layer) facing the underlying layer of connective tissue (the dermis). After a basal cell has divided into two daughter cells, one of the daughter cells—on average—remains in the basal cell layer, while the other gradually matures (keratinizes) as it migrates through the various layers of the epidermis. It reaches the surface as a fully keratinized cell without a nucleus, and is eventually shed. In the adult epidermis the number of cells lost from the surface in a given time is exactly balanced by the production of new cells in the basal cell layer. It is only in this manner that a constant thickness of the epidermis can be maintained. If a large number of epidermal cells are suddenly lost, e.g. after injury, the rate of cell division in the basal cell layer increases after a short lag time. After a period of time which depends on the degree of cell loss, the epidermis regains its former, normal, thickness. Large series of experiments have indicated that the balance between cell loss and cell renewal in the epidermis is biologically regulated according to the negative feedback principle. In such a system, the maturing cells continuously produce an inhibitor which diffuses down to the basal cell layer where it inhibits the rate of cell proliferation. The concentration of inhibitor in the basal cell layer is dependent on the number of mature, or maturing cells. Thus, when mature cells are lost from the surface, the concentration of inhibitor decrease, allowing the basal cells to divide at a faster rate. This regulatory mechanism seems to be active to a certain extent even in malignant tumors.

We have now discovered that the keratinizing cells produce an inhibitor (or a group of inhibitors) which is of peptide nature. We have also been able to isolate and determine the structure of such compounds. In particular we have purified, identified and chemically sunthesized pentapeptides which, when tested for biological activity in vivo, reversibly inhibit the rate of cell proliferation in the basal cell layer, e.g. upon administration to mice. Furthermore, in vitro experiments have demonstrated that cells of an established cell line are inhibited by these pentapeptides at very low concentrations. This cell line originates from mouse epidermis treated with a skin carcinogen (DMBA=dimethylbenzathracene). Continuous treatment in vitro will arrest cell proliferation completely for a period of several days in normal keratinizing epithelial cells, while transformed cells are only partially inhibited. In both cases the inhibition is completely reversible when the treatment is terminated. In vitro experiments have also demonstrated that both normal and transformed cells mature (keratinize) at a faster rate after a 24-hour treatment with one of the new pentapeptides. No toxic effects have been observed either in vitro or in vitro at the concentrations tested.

According to the invention there is provided a pentapeptide of the formula

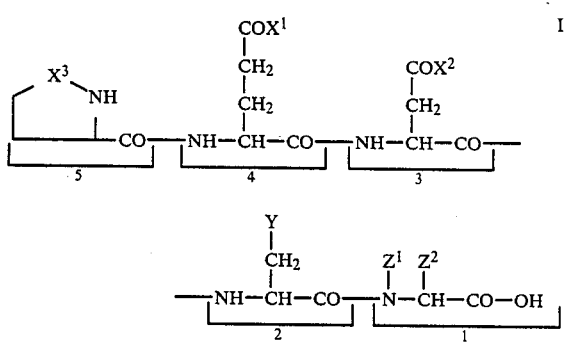

wherein
$X^1$ and $X^2$ are the same or different and are OH or $NH_2$,
Y is H or OH,
$X^3$ is CO or $CH_2$,
one of the groups $Z^1$ and $Z^2$ is H and the other H or $CH_3$,
all amino acid units being in the L-configuration, with the exception that the C-terminal amino acid unit is in the D-configuration when $Z^2$ is methyl,
and the C-terminal carboxyl group may be reduced to —$CH_2$—OH or in amide form, and cation complexes and salts thereof.

Suitable cation complexes are particularly complexes with $Zn^{++}$, $Ca^{++}$, $Mg^{++}$ and $Mn^{++}$. Suitable salts are acid addition salts, such as hydrochlorides and alkali, alkaline earth and amine salts which are physiologically acceptable. Thus, the following amino acid units may be included in the pentapeptide, counted from the C-terminal end:

| | | | |
|---|---|---|---|
| (1) | Glycine | (Gly) | [$Z^1 = Z^2 = H$] |
| | D-Alanine | (D-Ala) | [$Z^1 = H, Z^2 = CH_3$] |
| | Sarcosine | | [$Z^1 = CH_3, Z^2 = H$] |
| (2) | Alanine | (Ala) | [Y = H] |
| | Serine | (Ser) | [Y = OH] |
| (3) | Aspartic acid | (Asp) | [$X^2 = OH$] |
| | Asparagine | (Asn) | [$X^2 = NH_2$] |
| (4) | Glutamic acid | (Glu) | [$X^1 = OH$] |
| | Glutamine | (Gln) | [$X^1 = NH_2$] |
| (5) | Pyroglutamic acid | (pGlu) | [$X^3 = CO$] |
| | Proline | (Pro) | [$X^3 = CH_2$] |

In the following Table 1 in vivo results (change in mouse epidermal mitotic rate) have been described as example for four different new pentapeptides. The epidermal mitotic rate was measured for the first three hours after intraperitoneal injection of the new pentapeptides. Mitotic rate was determined by means of "Colcemid" (Demecolcine). A reduced rate was determined as a percentage in comparison with control animals from the same cage.

TABLE I

| Compound No. | Synthetic peptide (all amino acids in L-configuration) | Decrease in mitotic rate % | Peptide concentration, Moles of peptide injected per mouse |
|---|---|---|---|
| 1 | pGlu—Glu—Asp—Ser—Gly | 40–44 | $10^{-11}$–$10^{-14}$ |
| 2 | pGlu—Gln—Asp—Ser—Gly | 39 | $10^{-11}$ |
| 3 | pGlu—Glu—Asp—Ala—Gly | 36 | $10^{-13}$ |
| 4 | Pro—Glu—Asp—Ser—Gly | 23–26 | $10^{-11}$–$10^{-14}$ |

The new pentapeptide may, in a per se known manner, be incorporated in pharmaceutical compositions, e.g. as tablets, injection solutions, nose-spray compositions or suppositories.

The compounds of formula I may be prepared by subjecting a compound of formula I wherein carboxyl groups, amino groups and hydroxyl groups optionally present have been protected, to a treatment to remove the protective group(s).

During the synthesis of the pentapeptide it is e.g. possible to use one of the classical coupling methods published in the comprehensive and well known peptide literature. In general any reactive group (e.g. amino, hydroxyl and/or carboxyl) which shall not participate in a peptide bond, should be kept protected during the entire synthesis, and the last step will accordingly be a deprotection of a completely protected derivative of the desired final product. For the coupling steps in which the individual protected amino acids are bound together, several different known methods may be used, and these have been described in detail in the comprehensive literature regarding peptide synthesis. However, it is preferable here to prepare the different peptides by means of the socalled solid phase method, which is considered to be suitable for the preparation of oligopeptides and their analogues in a rapid manner and with good yields. In this method, which was first introduced by R.B. Merrifield in 1963, the growing peptide chain is kept attached to a solid polymer support, and the synthesis starts by binding the C-terminal amino acid to the polymer. The most common amino acids attached to a polymer support are today commercially available. The next amino acid is then coupled to this polymer-bound amino acid by a repeated cycle with deprotection, washing and coupling. In this manner the entire peptide is built up in a polymerbound form, and in the last step the final product is split off from the polymer by means of a suitable reagent (usually hydrofluoric acid, HF). In the following a typical example of a solid phase peptide synthesis is described.

Polymer support:

As solid carrier the following may, for example be used either
  chloromethylated polystyrene, cross-linked with 2% divinyl benzene, "mesh" size 200–400 with chloro substitution of 0.3–1.5 meq./g, or
  benzhydrylamine resin, also cross-linked with 2% divinylbenzene, "mesh" size 200–400 with $NH_2$ substitution of 0.3–1.5 meq./g.

In the following example a commercially available chloromethylated polymer to which amino group protected glycine has already been attached, is used.

EXAMPLE

Synthesis of pGlu-Glu-Asp-Ala-Gly 2 mmoles of Boc-Gly-Rx were used as starting material, and the following amino acids were added according to the usual principles for solid peptide synthesis:

| | |
|---|---|
| Boc—Ala | 1.13 g |
| Boc—Asp(OcHex) | 1.80 g |
| Boc—Glu(OcHex) | 1.90 g |
| pGlu | 0,90 g |

The following cycle was used:
  Wash 3 times with methylene chloride (1 min.)
  Wash once with 40% TFA (1 min.)
  Deprotect with 40% TFA (30 min.)
  Wash once with methylene chloride (1 min.)
  Wash once with ethanol (1 min.)
  Wash twice with methylene chloride (1 min.)
  Wash once with 10% TEA (1 min.)
  Neutralize with 10% TEA (10 min.)
  Wash 3 times with methylene chlorid (1 min.)
  Add 3 molar excess of Boc-amino acid and DCC
  Couple 3 hours.

In the last cycle the pyroglutamic acid was washed for 30 minutes with 10% TFA instead of with 40% since deprotection was not necessary.

Abbreviations:

| | |
|---|---|
| TFA = | trifluoroacetic acid |
| TEA = | triethylamine |
| Boc = | t-butoxy carbonyl |
| DCCf = | dicyclohexyl carbodiimide |
| Rx = | polymer support |
| OcHex = | cyclohexyloxy. |

Hydrogen fluoride treatment:

3,8 g of dried resin with pentapeptides attached thereto were placed in a Kel-F reaction vessel and wetted with approximately 10 ml of anisole. The reaction vessel was cooled by means of dry-ice/acetone, and 40 ml of HF were distilled over into the reaction vessel. The polymer with pentapeptide attached thereto was then stirred at 0° for 45 minutes, whereafter HF was removed by evaporation. The polymer was then washed with ether and extracted with 10% acetic acid, and the extract was lyophilized.

All the pentapeptides described herein have been prepared from the appropriate protected amino acids in a similar way. In Table II the physical-chemical data for six of these novel peptides are given.

TABLE II

Synthesized peptides - physical-chemical data

| | Amino acid analysis | | | | | | | TLC-Rf | | | Electrophoresis Rf | % of peptide in amino acid analysis | HPLC RT | |
|---|---|---|---|---|---|---|---|---|---|---|---|---|---|---|
| Comp. | Asp | Glu | Pro | Gly | Ala | Ser | $NH_3$ | S1 | S2 | S3 | | | S1 | S2 |
| 1 | 0.96 | 2.13 | — | 0.91 | — | 0.83 | — | 0.35 | | | $1.42^a$ | 96 | 9 | 6 |
| 2 | 0.95 | 1.97 | — | 1.08 | — | 0.82 | 0.89 | 0.31 | 0.26 | | 0.62 | 96 | 8.5 | 5 |
| 3 | 1.00 | 1.99 | — | 0.97 | 1.04 | — | — | 0.45 | | 0,18 | $1.58^a$ | 80 | 9 | 5 |
| 4 | 0.97 | 1.01 | 1.04 | 0.98 | — | 0.77 | — | 0.21 | 0.14 | | | | 6.4 | |
| 5 | 0.87 | 2.15 | —· | 0.98 | — | 0.69 | 1.70 | 0.39 | 0.46 | 0,37 | | 73.1 | | |

TABLE II-continued

| 6 | 1.01 | 2.31 | — | — | 0.83 | 0.85 | — | 0.38 | 0.24 | 96.9 |

Legend to Table II
Thin layer chromatography (TLC) - Systems
S1: Silica: n-BuOH:EtOAc:HOAc:$H_2O$ (1:1:1:1)
  Detection: o-tolidine
S2: Silica Fm: n-BuOH:Pyr:HOAc:$H_2O$(6:6:1,2:4,8)
  Detection: o-tolidine
S3: Silica F: n-BuOH:PyrHOAc:$H_2O$(15:10:3:12)
  Detection: o-tolidine
1–4: See table I
5: pGlu—Glu—Asp—Ser—Gly($NH_2$)
6: pGlu—Glu—Asp—Ser—D—Ala
Electrophoresis-system
Whatman 3 MM: Pyridine: acetic acid, pH 6.4, 1500 V, 1 hour
Detection: o-tolidine
Spot migrating towards the anode
Rf value with reference to arginine
$^a$Rf value with reference to picric acid.
High performance liquid chromatography (HCLC) - systems
S1: Column C-18
  Flow rate: 1 ml/min.
  Solvent: A-0.1% TFA, B-60% $CH_3CN$ in A
  Gradient: linear, 0 to 100% B in 40 min.
  Detector: UV 210 nm.
S2: Column: C-18
  Flow rate: 1 ml/min.
  Solvent: A-0.05 M $NaH_2PO_4$, B-60% $CH_3CN$ in A
  Gradient: linear, 0 to 100% B in 40 min.
  Detector: UV 210 nm
  Retention time (RT) in min.

We claim:
1. A pentapeptide, represented by the formula

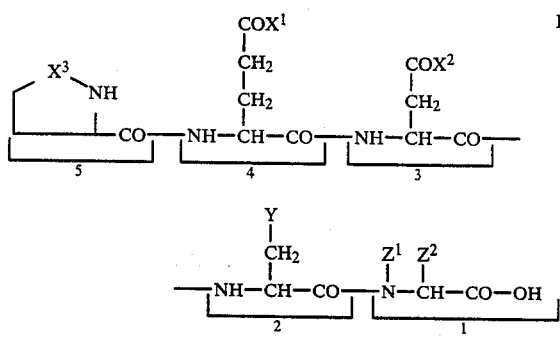

in which
$X^1$ and $X^2$ are the same or different and are OH or $NH_2$,
Y is H or OH,
$X^3$ is CO or $CH_2$,
one of the groups $Z^1$ and $Z^2$ is H and the other is H or $CH_3$,
all the amino acid units being in L-configuration, with the exception that the C-terminal amino acid unit is in D-configuration when $Z^2$ is methyl,
and the C-terminal carboxyl group may be in reduced form —$CH_2$—OH or be in amide form —CO—$NH_2$, and cation complexes and salts thereof.

2. Pentapeptide according to claim 1, represented by formula I in which $X^1$ is OH, $X^2$ is OH, $X^3$ is CO, Y is OH, $Z^1$ is H and $Z^2$ is H.

3. Pentapeptide according to claim 1, represented by formula I in which $X^1$ is $NH_2$, $X^2$ is OH, $X^3$ is CO, Y is OH, $Z^1$ is H and $Z^2$ is H.

4. Pentapeptide according to claim 1, represented by formula I in which $X^1$ is OH, $X^2$ is CO, Y is H, $Z^1$ is H and $Z^2$ is H.

* * * * *